United States Patent [19]

Kelman

[11] Patent Number: 4,955,902
[45] Date of Patent: Sep. 11, 1990

[54] DECENTERED INTRAOCULAR LENS

[76] Inventor: Charles D. Kelman, 721 Fifth Avenue, New York, N.Y. 10022

[21] Appl. No.: 436,300

[22] Filed: Nov. 13, 1989

[51] Int. Cl.$^5$ .............................................. A61F 2/16
[52] U.S. Cl. .................................................. 623/6
[58] Field of Search ............................................ 623/6

[56] References Cited

U.S. PATENT DOCUMENTS

| | | | |
|---|---|---|---|
| 2,834,023 | 5/1958 | Lieb | 623/6 |
| 4,253,200 | 3/1981 | Kelman | 623/6 |
| 4,524,468 | 6/1985 | Kelman | 623/6 |
| 4,596,578 | 6/1986 | Kelman | 623/6 |
| 4,608,049 | 8/1986 | Kelman | 623/6 |
| 4,678,469 | 7/1987 | Kelman | 623/6 |
| 4,871,363 | 10/1989 | Kelman | 623/6 |

OTHER PUBLICATIONS

"Galilean Telescope Using the Anterior Chamber Implant as Eye-Piece: A low-Visual-Acuity Aid for Masular Lesions", *Intra-Ocular Lenses and Implants* (Book) by Peter Choyce H. K. Lewis & Co. Ltd., London 1964, pp. 156–161.

*Primary Examiner*—Ronald Frinks
*Attorney, Agent, or Firm*—Darby & Darby

[57] ABSTRACT

Decentered intraocular lens, usable to correct high myopia of an intact natural lens in an eye having a decentered pupil, by insertion through an eye incision and implanting in the anterior chamber at minimum risk of contacting the natural lens. The intraocular lens includes a lens body having a thickened outer edge and a concave face, and a pair of opposed haptics each terminating in a transverse edge having a pair of laterally spaced lobes to engage adjacent eye tissue at a corresponding pair of spaced tissue points, the transverse edges being of unequal length and arranged at respective distances from the lens body so that the lobes lie in a circle whose center is eccentric to the lens body optical axis, to position the lens body in spaced relating to the natural lens, decentered relative to the circle and eye optical axis and centered relative to the decentered pupil, with the lens body outer edge masked by the iris to inhibit transmission thereat of entering edge glare causing light rays.

3 Claims, 2 Drawing Sheets

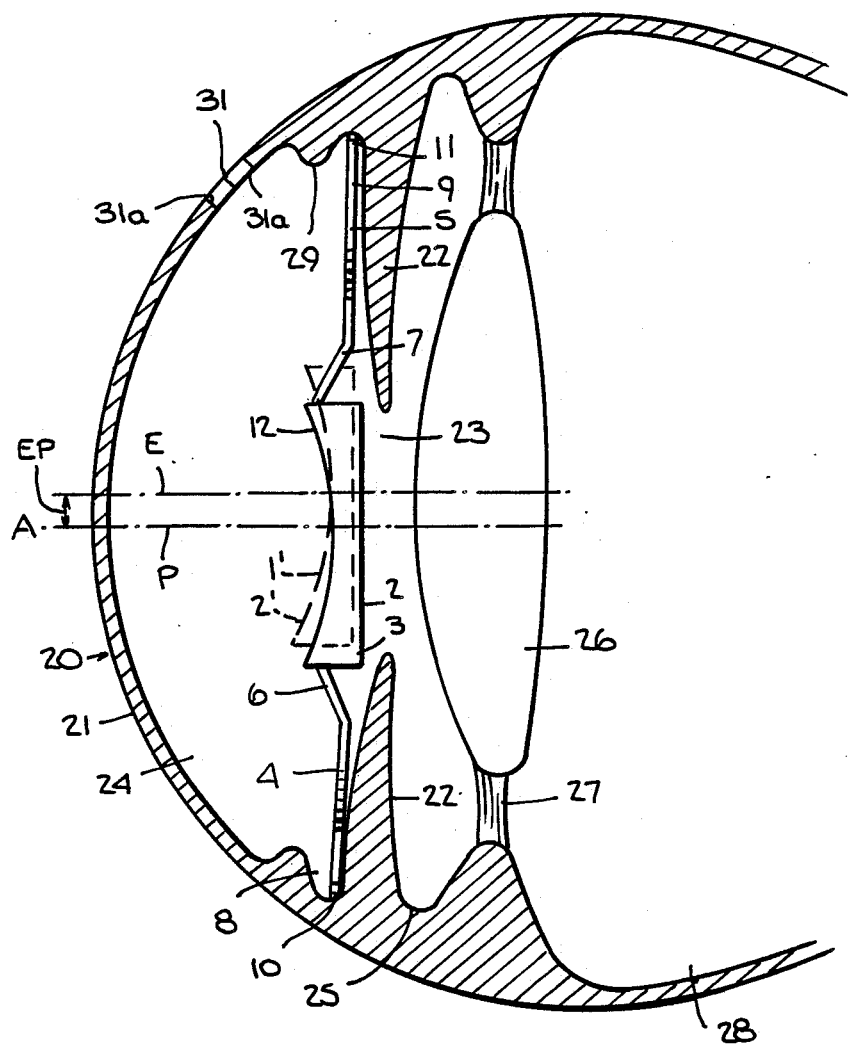

DECENTERED INTRAOCULAR LENS

FIELD AND BACKGROUND OF THE INVENTION

This invention relates to a decentered intraocular lens, and more particularly to such an artificial lens to correct high myopia of an intact natural lens in an eye having a decentered pupil. The artificial lens is implanted in the anterior chamber in front of the natural lens and centered relative to the pupil, its lens body having differentially sized haptics to insert it safely without damaging the natural lens and maintain it in pupil centered position, with its outer edge sufficiently masked by the iris to inhibit edge glare.

This invention is an improvement over applicant's earlier teaching in U.S. application Ser. No. 222,133 filed July 21, 1988, now U.S. Pat. No.4,871,363 the disclosure of which is hereby incorporated herein.

That earlier teaching concerns an intraocular lens, inserted via a corneal incision and implanted in the anterior chamber, e.g. to treat high myopia. The unit has a lens body centered by opposed leading and trailing haptics, each terminating in a transverse edge with a pair of laterally spaced contact lobes to engage tissue in the angle groove between the scleral spur and iris, per four point fixation technique, to seat the unit centered relative to the pupil and eye axis. The unit has a short edge trailing haptic for safe implanting via a minimum size incision without contacting the natural lens. On inserting the leading haptic and lens body, the trailing haptic is slightly pressed to clear the incision and be seated.

However, that earlier teaching does not concern the problem of implanting an intraocular lens in the anterior chamber of an eye having a decentered pupil, so that the centered lens body is decentered relative to the iris, and causes objectionable edge glare, as where the lens body is a high myopia corrective lens, i.e. having a thickened outer edge, which does not completely or at least not sufficiently overlap the iris, and thus permits light rays striking the lens body edge to produce edge glare transmitted to the retina.

U.S. Pat. No. 4,253,200 to Kelman shows a posterior chamber intraocular lens with a lens body and pair of haptics, one radially longer than the other, but they do not have opposing contact lobe pairs for four point fixation, nor is the lens body precisely decentered relative to the optical axis of the eye, or constructed to correct natural lens high myopia in an eye having a decentered pupil causing lens body edge glare. The unit replaces the natural lens, after its extracapsular removal, and is located behind the iris with the longer haptic seated in the ciliary sulcus and the shorter one seated in the capsular bag from which the natural lens has been removed.

SUMMARY OF THE INVENTION

It is an object of the invention to provide a decentered intraocular lens, insertable via a minimum size incision at minimum patient risk of touching the intact natural lens, for stable fixation in the anterior chamber of an eye having a decentered pupil, to correct high myopia of the natural lens, with the lens body centered relative to the decentered pupil, so that its edge is masked by the iris against edge glare.

According to the invention, a decentered intraocular lens is provided that is usable as an anterior chamber lens to correct high myopia of an intact natural lens in an eye having a decentered pupil relative to the eye optical axis, by insertion into the eye through a minimum size incision and implantation in the anterior chamber, comprising a lens body with an optical axis, a thickened outer edge and a concave face to correct high myopia of the natural lens, and a diameter at least as large as the decentered pupil average diameter, and a pair of diametrically opposed resiliently deflectable position fixation haptics extending outwardly from the lens body.

The haptics constitute a leading haptic and a trailing haptic, each comprising a pliable strand having a stem portion or stem attached to the lens body and a limb portion or limb extending from the stem and terminating in a transverse edge portion or edge disposed crosswise of a longitudinal diametric line passing through the lens body and intersecting both transverse edges. Each transverse edge has a pair of laterally spaced apart and outwardly projecting contact lobes at the corresponding transverse ends thereof to engage an adjacent eye tissue portion at a corresponding pair of spaced tissue points.

The trailing haptic transverse edge has a length of about 2–3 mm and is arranged at a predetermined longer distance from the lens body along the diametric line than that of the leading haptic transverse edge concordant to the decentering increment of the pupil axis relative to the eye optical axis, and the lens body diameter and leading haptic transverse edge each have a length substantially larger than about 2–3 mm.

The pairs of lobes lie in a circle having its center eccentrically spaced from the lens body optical axis a predetermined increment corresponding substantially to such pupil axis decentering increment, and form two generally diametrically opposed pairs of laterally spaced apart fixation points, to position the intraocular lens in the anterior chamber in spaced relation to the natural lens with the lens body optical axis correspondingly decentered relative to the circle and eye optical axis and substantially coincident to the axis of the decentered pupil, and with the lens body thickened outer edge substantially centered relative to the pupil and masked by the adjacent edge of the iris sufficiently to inhibit transmission thereat of entering edge glare causing light rays.

Preferably, the lens body diameter is about 5–6 mm, the leading haptic transverse edge length is about 5–6 mm, the longitudinal dimension in generally diametric direction between the opposed pairs of lobes is about 12.5 mm, and each haptic forms a sinusoidal continuous strand having its stem attached to the lens body in the vicinity of the lens body periphery.

To correct natural lens myopia, the lens body normally has a thickened outer edge and a concave face, but such construction causes edge glare in an eye having a decentered pupil. According to the invention, the lens body diameter is at least as large as the average diameter of the pupil or iris inner edge, at least under average light conditions, and the lobes implant the intraocular lens with the lens body optical axis generally coincident to the decentered pupil axis and decentered relative to the eye optical axis, so that the lens body outer edge is masked by the iris to inhibit such edge glare.

According to the invention, a method is also provided for implanting the decentered intraocular lens to correct such intact natural lens high myopia in an eye having a decentered pupil relative to the eye optical axis, comprising insertng the intraocular lens into the anterior chamber via an incision of length corresponding substantially to the lens body diameter, and located slightly anteriorly spaced from the scleral spur and slightly closer than the scleral spur to the eye axis, to engage the opposed haptic transverse edges in the anterior angle groove at corresponding opposed eye tissue portions of such groove, whereby to position the intraocular lens in the above stated orientation, at minimum risk of contact with the natural lens by the intraocular lens during the implantation.

BRIEF DESCRIPTION OF THE DRAWINGS

Other objects of the invention will become apparent from the within specification and accompanying drawings, in which:

FIG.3 is a schematic exaggerated sectional view of an eye having a decentered pupil, corresponding to FIG. 2 and showing the implanting of the decentered lens of the invention in the anterior chamber on insertion through such a corneal incision.

DESCRIPTION OF THE PREFERRED EMBODIMENTS

Figure 1:
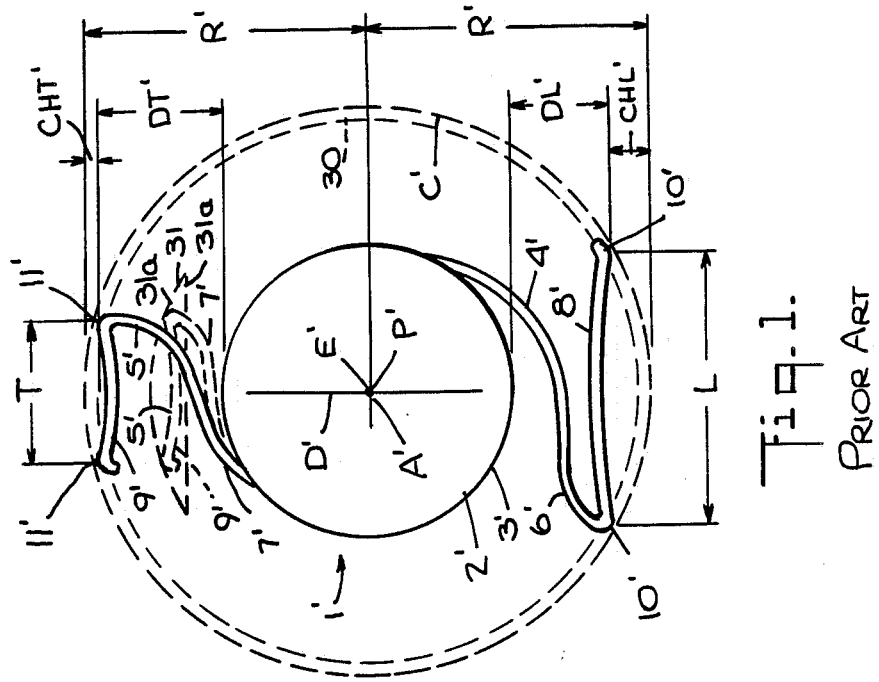
FIG.1 is a schematic exaggerated view of the anterior side of a PRIOR ART centered intraocular lens having a centered lens body and pair of opposed haptics outwardly terminating in unequal length transverse edges, each with a pair of laterally spaced lobes, shown in the anterior chamber of an eye having an intact natural lens, and centered relative to the eye axis, on insertion through a minimum size corneal incision (in phantom), for comparison with the intraocular lens of the invention.

Referring to the drawings, and initially to FIG. 1, a PRIOR ART centered intraocular lens 1' is shown, such as is contemplated in applicant's said earlier teaching in U.S. application Ser. No. 222,133, formed of lens body or optic 2' with a peripheral edge 3', and a pair of diametrically opposed position fixation haptics, i.e. leading haptic 4' and trailing haptic 5', of unequal size and shape attached to optic 2' at peripheral edge 3' and arranged to keep optic 2' centered relative to lens 1' to position it in the eye with optic axis A' coincident to pupil axis P' and eye axis E'.

Haptics 4' and 5' are resiliently deflectable strands, and repectively include opposed leading and trailing stems 6' and 7', attached to optic 2' and extending radially outwardly from peripheral edge 3', and terminating in transverse leading and trailing limbs 8' and 9' extending from stems 6' and and 7'.

Limbs 8' and 9' form transverse edge portions or edges respectively having at their transverse or crosswise ends the laterally spaced apart pairs of radially outwardly projecting leading and trailing contact lobes 10',10' and 11',11' which lie in a circle C' of radius R' having its center coincident to axis A' to engage eye tissue portions in angle groove 30 (shown in phantom) in the anterior chamber of the eye, when implanted.

Lobes 10',10' and 11',11' space the intermediate spans of transverse edges 8' and 9' from the adjacent eye tissue.

Transverse edges 8' and 9' extend crosswise of a longitudinal diametric line passing through optic 2', e.g. at axis A', and intersecting edges 8' and 9', so that lobe pairs 10', 10' and 11',11' at their respective transverse ends are arranged to engage opposed eye tissue portions at corresponding respective pairs of spaced tissue points, to form two diametrically opposed pairs of laterally spaced fixation points to position lens 1' in the eye. This is a modification of the known "Quadraflex" lens arrangement permitting relatively stable four point fixation of the unit in the eye, with the pairs of fixation points being unequally laterally spaced in dependence upon the unequal lateral spacing of lobes 10',10' and 11'.

Typically, optic 2' has a diameter of about 5–6 mm, limb 8' has a transverse length of about 5–6 mm, limb 9' has a transverse length of about 2–3 mm, and the lobes have a radius of about 0.125 or 0.25 mm, for a 4.75–5.75 or 4.5–5.5 mm lateral distance L' between leading lobes 10',10', center to center (i.e. between the lobe crests), and a 1.75–2.75 or 1.5–2.5 mm lateral distance T' betweem trailing lobes 11', 11', center to center, depending on whether their radius is 0.125 or 0.25 mm, and a longitudinal dimension D' of about 12.5 mm diametrically between lobe pairs 10',10' and 11',11'.

To implant lens 1', e.g. in the anterior chamber of an eye to correct high myopia of an intact natural lens, it is typically inserted through a corneal incision 31 (shown in phantom) of length just sufficient for optic 2' to pass therethrough, by first passing leading haptic 4' between its lips 31a, next optic 2', seating leading lobes 10',10' against the eye tissue in angle groove 30 (shown in phantom) posteriorly of the scleral spur and anteriorly of the iris, and then pressing the exposed trailing haptic 5' therethrough (shown in phantom).

As implanted in the anterior chamber, optic 2' is centered in lens 1', circle C' and angle groove 30, with axis A' coincident to centered pupil axis P' and eye axis E', so that optic 2' is centered relative to the pupil and iris by haptics 4' and 5' of such configuration, i.e. regarding the differential lengths of edges 8' and 9' and the radial distances of lobes 10',10' and 11',11' from axis A' and/or from peripheral edge 3', that optic 2' is kept in concerntric orientation.

As leading edge 8' is longer than trailing edge 9', the leading side chord of circle C' intersecting the crests of lobes 10',10', which chord is roughly the same length as edge 8',is correspondingly longer than the trailing side chord intersecting the crests of lobes 11',11', which chord is likewise roughly the same length as edge 9'.

Portion CHL' of diameter 2R' of circle C' radially outwardly of longer leading side chord or edge 8' is likewise, but only slightly, longer in radial direction than portion CHT' of diameter 2R' radially outwardly of shorter trailing side chord or edge 9'. Concordantly, portion DL' of diameter 2R' radially inwardly of longer chord or edge 8' and terminating at its adjacent portion of peripheral edge 3' is likewise, but only slightly, shorter in radial direction than portion DT' of diameter 2R' radially inwardly of shorter chord or edge 9' and terminating at its adjacent portion of peripheral edge 3'.

As optic 2' is centered in circle C' by lobes to arrange axis A' coincident with axes P' and E', composite radial distance (CHL'+DL') equals composite radial distance (CHT'+DT'), and their sum plus the optic 2' diameter equals diameter 2R'. Dimension D' is slightly shorter than diameter 2R' by the sum of CHL' and CHT'.

Given the order of these dimensions in terms of an eye, CHL' and CHT' are very small.

As haptics 4' and 5' are under slight radial compression when engaged in angle groove 30 for stable fixation of lens 1', diameter 2R' of lens 1' in undeflected state is slightly larger than the angle groove diameter to allow therefor.

For an angle groove diameter of about 12.5 mm, circle C' diameter 2R' maybe about 13 mm, so that for an optic 2' diameter of about 5-6 mm, DL' and CHL' may be about 3.7-3.2 mm and 0.3 mm, and DT' and CHT' about 3.8-3.3 mm and 0.2 mm, respectively, D' being about 12.5 mm whether optic 2' diameter is 5 or 6 mm, as generally CHL' and CHT' will correspondingly remain 0.3 mm and 0.2 mm, for a given set of L' and T' values.

It will be noted that while the haptics are of pliable material, they are not permanently deformable after fabrication, as by attempted bending to impart kinks thereto or otherwise change their shape to change their radial lengths, i.e. the distance beteeeen the center of circle C' and the repective edges 8' and 9'. This would undermine the purpose of the critically precisely dimensioned intraocular lens to serve permanently in the eye in a predetermined position, at minimum risk of dislodging, sagging or deviating from alignment with the eye optical axis. Thus, optic 2' cannot simply be rendered decentered to circle C' after fabrication of lens 1'.

The invention provides a modified construction and cognate implanting method for use in an eye having a decentered pupil.

Figure 2:
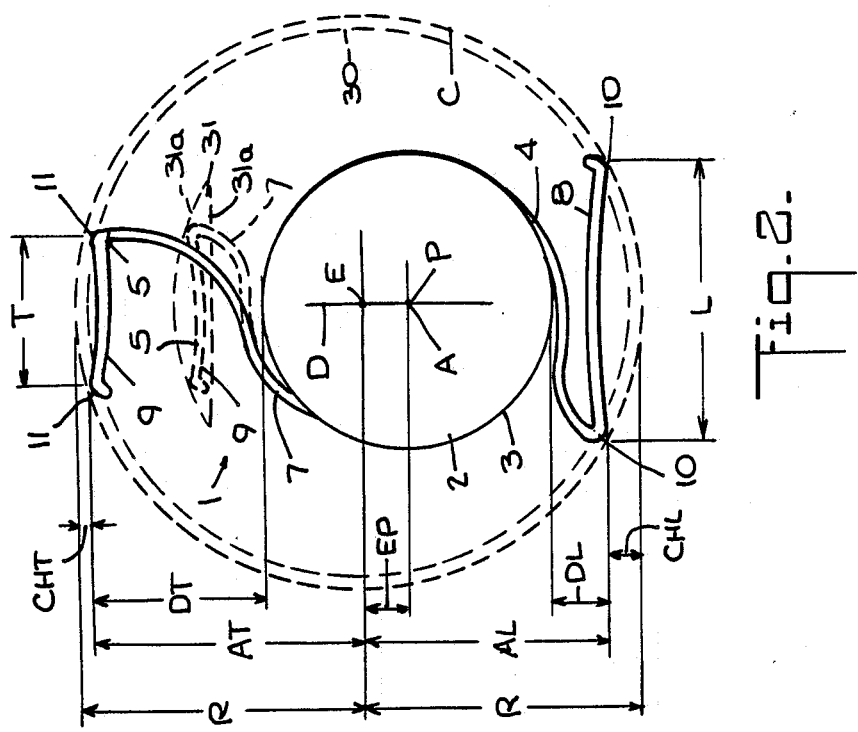
FIG. 2 is a schematic exaggerated view similar to FIG. 1, showing a decentered intraocular lens according to the invention, having a decentered lens with analogous haptics, shown in the anterior chamber of eye having an intact natural lens and decentered pupil, with the lens body centered relative to the pupil and decentered relative to the eye axis.

As shown in FIGS. 2-3, intraocular lens 1 of the invention, is constructed as a decentered lens for the intact natural lens of an eye having a decentered pupil, and has like parts of like sizing to those of lens 1' of FIG. 1, for the same purposes, as more fully disclosed in applicant's said earlier teaching in Ser. No. 222,133, except for the haptic differential radial arrangement and sizing to keep the lens body decentered relative to the normal concentric orientation.

Decentered lens 1 has a lens body or optic 2, i.e. a high myopia corrective optic, with a concave face 12 and thickened outer or peripheral edge 3 to which the pair of diametrically opposed position fixation haptics, i.e. leading and trailing haptics 4 and 5, is attached, e.g. integrally, comprising resiliently defectable means such as sinusoidal continuous, pliable strands repectively having radially outwardly extending leading and trailing stems 6 and 7 attached to optic 2 in the vicinity of peripheral edge 3, and transverse leading and trailing limbs 8 and 9 extending outwardly from stems 6 and 7 and forming transverse edges containing laterally spaced apart leading and trailing contact lobe pairs 10,10 and 11,11.

Edges 8 and 9 differ from edges 8' and 9' of lens 1', in being arranged at radial distances from optic 2 to keep central optic axis A eccentric to the center of circle C of radius R in which the opposed pairs of lobes 10,10 and 11,11 lie, and thus eccentric or decentered relative to eye axis E, yet centered relative to axis P of the particular decentered pupil and the iris, when implanted via angle groove 30 (FIGS. 2-3).

Diameter 2R of circle C corresponds to diameter 2R' of circle C'; lateral distances L and T and the radius sizing of lobes 10,10 and 11,11 correspond to distances L' and T' and the radius sizing of lobes 10',10' and 11',11'; and radial distances CHL and CHT correspond to distances CHL' and CHT'. However, radial distances DL and DT do not correspond to distances DL' and DT', as optic 2 is radially shifted toward leading edge 8 and away from trailing edge 9 by a predetermined eccentricity increment EP of its axis A from the center of circle C, and from eye axis E, concordant with the particular eccentricity increment of pupil axis P from axis E.

Axis A is spaced from leading edge 8, i.e. the coresponding leading side chord intersecting the crests of lobes 10,10, by shorter radial distance AL, and from trailing edge 9, i.e. the corresponding trailing side chord intersecting the crests of lobes 11,11 by longer radial distance AT, so that radial distance DL is shorter than DL' by increment EP, and distance DT is longer than DT' by increment EP, while radial distances CHL and CHT are the same as CHL' and CHT', as all other dimensions are the same, including 2R and 2R' and D and D'.

FIG. 3 shows an eyeball 20 having a cornea 21, and iris 22 which in this case is decentered, thus forming a decentered adjustable opening or pupil 23, and which separates anterior chamber 24 from posterior chamber 25, and an intact natural eye lens 26 located in posterior chamber 25 by zonules or suspensory ligament and fibers 27 attached to its periphery. Anterior chamber 24 has a circumferential scleral spur 29 anteriorly of iris 22, between which is defined circumferential angle groove or "angle" 30 typically of about 12.5 mm diameter.

In the usual case, pupil 23 is decentered by an increment EP of about 0.5-1 mm, i.e. pupil axis P is eccentric to eye axis E by increment EP, and normally in nasal direction.

The orientation of FIGS. 1-3 may thus be regarded with the leading side of circle C' or C at leading haptic 4' or 4 adjacent the nasal side of the head and the trailing side of circle C' or C at trailing haptic 5' or 5 adjacent the temporal side, with incision 31 also located at the temporal side to permit easy manipulation of lens 1 for insertion without interference from the nose, and seating of lobes 10,10 in the angle groove 30 distal portion near the nose and lobes 11,11 in the angle groove 30 proximate portion near incision 31.

As lens 1 is implanted in anterior chamber 24 to correct high myopia of intact natural lens 26, and thus, to prevent damage thereto, will be maintained spaced therefrom, and desirably will also be spaced from iris 22 to permit unhindered iris adjustment, stems 6 and 7 are preferably offset axially relative to the main plane of optic 2 in a direction posteriorly (FIG. 3), to space optic 2 anteriorly safely from natural lens 26 and iris 22, yet with optic 2 decentered relative to eye axis E and centered relative to decentered pupil 23.

As is clear from FIG. 3, in carrying out the implantation procedure, corneal incision 31 (c.f. FIGS. 1 and 2) is made of a length corresponding to the optic 2 diameter, e.g. about 5-6 mm, and in crosswise direction at a spherical level relative to eyeball 20 slightly anteriorly spaced from scleral spur 29 and thus slightly closer than scleral spur 29 to optical axis E. The distance from incision 31 to the farthest point in 12.5 mm diameter angle groove 30, e.g. near the nose, is normally less than 13 mm, i.e. diameter 2R of lens 1, and is typically only 11 mm, due to the anteriorly off set location of incision 31 relative to the plane passing through angle groove 30.

Lens 1 is inserted through incision 31 by passing leading haptic 4 between its lips 31a, e.g. by "snaking" edge 8 and stem 6 therethrough, next passing optic 2 therethrough, and then moving inserted leading haptic 4 so that edge 8 enters the most distant portion of angle groove 30 near the nose and lobes 10,10 engage a corresponding pair of spaced tissue points in angle groove 30, while trailing edge 9 extends outwardly from incision 31 about 2 mm. Then, trailing haptic 5 is gently pressed under minimum pressure just sufficient to deflect edge 9 through lips 31a, while slightly tilting edge 9 to engage lobes 11,11 with the adjacent angle groove 30 tissue portion near the temporal side of the head to implant lens 1.

The short 2-3 mm length of limb 9 is relatively critical, as it determines the center to center spacing of lobes 11,11, i.e. the length from the crest of one lobe to that of the other. While this crest to crest length between lobes 11,11 is actually slightly less than that between the transverse ends of edge 9, this slight difference is negligible given the very small lobe radius of curvature, e.g. about 0.125-0.25 mm, so that for an edge 9 length of about 2-3 mm, the crest to crest spacing of its lobes is about 1.5-2.75 mm. Hence, the length of edges 8 and 9 and their lobe spacing may be regarded as the same, i.e. about 2-3 mm for edge 9 and 5-6 mm for edge 8.

A trailing edge 9 substantially shorter than about 2 mm would eliminate the advantage of separated two-point contact of its lobes with the eye tissue points and result in unduly short line contact tantamount to a single gross point contact of poor fixation stability. A trailing edge 9 substantially longer than about 3 mm would not allow the surgeon to take full advantage of "gaping" incision 31 and would require intense squeezing and distortion of lens 1 risking natural lens injury.

The above insertion procedure can thus be carried out under minimum deflection of lens 1, due to the resiliently deflectable nature of haptics 4 and 5, and minimum risk of disturbance or dislodging of the previously positioned lobes 10,10 in angle groove 30, or of twisting optic 2 out of its generally continuously maintained parallel relation to natural lens 26, and in turn under maximum inhibition of contact with natural lens 26 by any part of lens 1 during the implanting.

For an optic 2 diameter of about 5-6 mm, e.g. 5 mm, and a circle C of about 13 mm diameter 2R, in the case of a 0.5 mm decentered pupil, the composite radial distance (CHT+DT) may be about 4.5-4 mm and (CHL+DL) about 3.5-3 mm, and in the case of a 1 mm decentered pupil as regards the same dimensions, (CHT+DT) may be about 5-4.5 mm and (CHL+DL) about 3-2.5 mm.

Assuming a constant distance of about 0.2 mm for CHT and 0.3 mm for CHL, the remainder of the composite radial distance will be the lengths of DT and DL. However, it is clear from FIG. 2 that the differential between CHT and DT, and between CHL and DL, depend on T and L, as these roughly correspond to the distances between their lobe pairs, i.e. the chords intersecting the spaced lobe crests, which determine the radical division point between CHT and DT, and between CHL and DL.

As these dimensions are very small, changes in length of edges 9 and 8, and thus of T and L, will only result in slight changes in CHT and CHL, and DT and DL, so that CHT and CHL may be regarded as of constant lengths of about 0.2 mm and 0.3 mm, respectively, totaling about 0.5 mm, the remainder being DT and DL, depending on T and L, and diameter 2R of circle C, e.g. 13 mm, and optic 2 diameter, e.g. 5 or 6 mm.

Thus, normally trailing haptic 5 will have a laterally shorter edge 9 and a radially longer stem 7, and leading haptic 4 a laterally longer edge 8 and a radially shorter stem 6, so that longer stem 7 will advantageously provide haptic 5 as the more flexible haptic, enhancing its easy final insertion via incision 31 without fear of touching natural lens 26.

As is clear from FIGS. 2-3, once lens 1 is inserted, haptics 4 and 5 engage angle groove 30 to keep optic 2 centered relative to decentered pupil 23 and spaced from natural lens 26, with optic axis A coincident to pupil axis P and eccentric by increment EP to eye axis E, as compared with lens 1' in FIG. 1 in whcih the eye has a centered pupil and optic 2' is centered in lens 1' and also centered relative to the pupil, with axis A' coincident to both axis P' and axis E'.

As optic 2 has a thickened outer edge 3, e.g. about 0.75-1.25 mm, preferably about 1 mm, in the axis A direction, and a concave face, e.g. for a center thickness of about 0.35-0.65 mm, preferably about 0.5 mm, to provide a high myopia corrective system, it is subject to objectionable edge glare due to transmisson of entering edge glare causing light rays through the thickened edge that reach the natural lens and retina.

Normally, this glare is not a problem with a convex optic as it has a thin outer edge, e.g. 0.1 mm, not with a thickened outer edge optic implanted in the anterior chamber of an eye with a centered pupil as the iris masks the optic edge. While artificial light masking means are known to inhibit such edge glare, as per applicant's U.S. Pat. Nos. 4,596,578; 4,608,409; and 4,678,469, these involve other considersations and are mostly only used where the intraocular lens replaces the natural lens.

In the case of decentered pupil 23, implanting centered lens 1' in anterior chamber 24, as shown in phantom in FIG. 3, will position axis A' coincident to eye axis E but eccentric by increment EP to pupil axis P, so that its thickened outer edge 3' will overlap unevenly with the adjacent edge of iris 22, causing a portion of outer edge 3' to lie in the opening span of pupil P, and permit transmission thereat of entering edge glare causing light rays that will reach natural lens 26 and the retina. This cannot be avoided by using a larger diameter optic sufficient to prevent such uneven overlap, as that would require an objectionably larger incision, and the incision size must be kept as small as possible to minimize patient trauma.

As lens 1 has a decentered optic 2, and as all optics are desirably sized to be at least as large as the pupil opening, and thus at least as large as the adjacent edge of the iris. i.e. at least under average light conditions, if not decreased light conditions at increased pupil dilation, upon implanting lens 1 in anterior chamber 24, thickened outer edge 3 will be sufficiently masked by the adjacent edge of iris 22 to inhibit transmission thereat of glare causing light rays. Of course, eccentric increment EP of the patient is first determined and lens 1 then constructed with a matching eccentric increment.

The optic may be made of polymethylmethacrylate (PMMA) or other suitable light focusing optical material, and the haptics of shape retaining, limitedly resilient, deflectable material, such as a suitable plastic, e.g. polymethylmethacrylate (PMMA). All materials used for the intraocular lens must be compatible with the internal eye environment, and thus non-toxic.

It will be noted that the specification and drawings are set forth by way of illustration and not limitation, and that various modifications and changes may be made therein without departing from the spirit and scope of the invention which is to be limited solely by the scope of the claims.

What is claimed is:

1. Decentered intraocular lens usable as an anterior chamber lens to correct high myopia of an intact natural lens in an eye having a decentered pupil relative to the eye optical axis, by insertion into the eye through a minimum size incision and implantation in the anterior chamber, comprising a lens body having an optical axis, a thickened outer edge and a concave face to correct high myopia of the natural lens, and a diameter at least as large as the average diameter of the decentered pupil, and a pair of generally diametrically opposed resiliently deflectable position fixation haptics extending outwardly from the lens body, the haptics constituting a leading haptic and a trailing haptic, each comprising a pliable strand having a stem portion attached to the lens body and a limb portion extending from the stem portion and terminating in a transverse edge portion disposed crosswise of a longitudinal diametric line passing through the lens body and intersecting both transverse edge portions, each transverse edge portion having a pair of laterally spaced apart and outwardly projecting contact lobes at the corresponding transverse ends thereof to engage an adjacent eye tissue portion at a corresponding pair of spaced apart tissue points, the trailing haptic transverse edge portion having a length of about 2-3 mm and being arranged at a predetermined longer distance from the lens body along the diametric line than that of the leading haptic transverse edge portion concordant to the decentering increment of the pupil axis relative to the eye optical axis, and the lens body diameter and leading haptic transverse edge portion each having a length substantially larger than about 2-3 mm, so that the pairs of contact lobes lie in a circle having its center eccentrically spaced from the lens body optical axis a predetermined increment corresponding substantially to said decentering increment of the pupil axis, and form two generally diametrically opposed pairs of laterally spaced apart fixation points, to position the intraocular lens in the anterior chamber in spaced relation to the natural lens with the lens body optical axis correspondingly decentered relative to the circle and eye optical axis and substantially coincident to the axis of the decentered pupil, and with the lens body thickened outer edge substantially centered relative to the pupil and masked by the adjacent edge of the iris sufficiently to inhibit transmission thereat of entering edge glare causing light rays.

2. Lens of claim 1 wherein the lens body diameter is about 5-6 mm, the leading haptic transverse edge portion length is about 5-6 mm, the longitudinal dimension in generally diametric direction between the opposed pairs of contact lobes is about 12.5 mm, and each haptic is formed as a generally sinusoidal continuous strand having a stem portion attached to the lens body in the vicinity of the lens body periphery.

3. Method of implanting the lens of claim 1 to correct high myopia of an intact natural lens in an eye having a decentered pupil relative to the eye optical axis, comprising inserting the intraocular lens into the anterior chamber of the eye through an incision of length corresponding substantially to the lens body diameter, and located slightly anteriorly spaced from the scleral spur and slightly closer than the scleral spur to the eye optical axis, to engage the generally diametrically opposed transverse edge portions of the haptics in the anterior angle groove at corresponding generally diametrically opposed eye tissue portions of such groove, whereby to positon the intraocular lens in spaced relation to the natural lens and substantially coincident to the axis of the decentered pupil, and with the lens body thickened outer edge substantially centered relative to the decentered pupil and masked by the adjacent edge of the iris sufficiently to inhibit transmission thereat of entering edge glare causing light rays, under minimum risk of contact with the natural lens by the intraocular lens during the implantation.

* * * * *